United States Patent
Han et al.

(10) Patent No.: US 10,440,319 B2
(45) Date of Patent: Oct. 8, 2019

(54) DISPLAY APPARATUS AND CONTROLLING METHOD THEREOF

(71) Applicant: SAMSUNG ELECTRONICS CO., LTD., Suwon-si, Gyeonggi-do (KR)

(72) Inventors: Ji-youn Han, Seoul (KR); Sung-hyun Jang, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/450,537

(22) Filed: Mar. 6, 2017

(65) Prior Publication Data

US 2018/0091772 A1    Mar. 29, 2018

(51) Int. Cl.
| | |
|---|---|
| H04N 7/14 | (2006.01) |
| A61B 5/00 | (2006.01) |
| G06F 3/01 | (2006.01) |
| G06K 9/00 | (2006.01) |
| G06K 9/78 | (2006.01) |

(Continued)

(52) U.S. Cl.
CPC .......... *H04N 7/147* (2013.01); *A61B 5/0077* (2013.01); *A61B 5/1072* (2013.01); *A61B 5/1077* (2013.01); *A61B 5/1079* (2013.01); *A61B 5/1114* (2013.01); *A61B 5/1123* (2013.01); *A61B 5/1128* (2013.01); *A61B 5/6801* (2013.01); *A61B 5/6887* (2013.01); *A61B 5/742* (2013.01); *A61B 5/7425* (2013.01); *G06F 3/017* (2013.01); *G06F 3/0484* (2013.01); *G06K 9/00362* (2013.01); *G06K 9/78* (2013.01); *H04N 5/23293* (2013.01); *A47F 2007/195* (2013.01); *A47G 1/02* (2013.01); *G06F 2203/04806* (2013.01)

(58) Field of Classification Search
USPC ...................................... 348/14.03
See application file for complete search history.

(56) References Cited

U.S. PATENT DOCUMENTS

| | | | |
|---|---|---|---|
| 8,624,883 B2* | 1/2014 | Vilcovsky | G02B 5/08 |
| | | | 345/204 |
| 2002/0196333 A1* | 12/2002 | Gorischek | A45D 44/005 |
| | | | 348/61 |

(Continued)

FOREIGN PATENT DOCUMENTS

| | | |
|---|---|---|
| JP | 2005-005791 | 1/2005 |
| JP | 2009-110493 | 5/2009 |

(Continued)

OTHER PUBLICATIONS

PCT/KR2017/005291 Written Opinion dated Aug. 21, 2017.

(Continued)

*Primary Examiner* — Amal S Zenati
(74) *Attorney, Agent, or Firm* — Nixon & Vanderhye P.C.

(57) ABSTRACT

A display apparatus is disclosed. The display apparatus may include a display configured to operate as at least one of a screen and a mirror, a photographing unit configured to generate a photographed image in which a subject present in a display direction of the display is photographed, and a processor configured to control the display in order for a first area of the display operate as a screen displaying part of the photographed image and a second area other than the first area to operate as a mirror.

18 Claims, 14 Drawing Sheets

(51) Int. Cl.
*H04N 5/232* (2006.01)
*A61B 5/107* (2006.01)
*A61B 5/11* (2006.01)
*G06F 3/0484* (2013.01)
*A47G 1/02* (2006.01)
*A47F 7/19* (2006.01)

(56) References Cited

U.S. PATENT DOCUMENTS

| | | | |
|---|---|---|---|
| 2007/0040033 A1* | 2/2007 | Rosenberg | A47G 1/02 235/462.36 |
| 2008/0055730 A1 | 3/2008 | Lin et al. | |
| 2011/0018864 A1 | 1/2011 | Ishibashi | |
| 2011/0228155 A1* | 9/2011 | Lee | A45D 42/00 348/333.01 |
| 2011/0298910 A1 | 12/2011 | De Haan et al. | |
| 2013/0148002 A1 | 6/2013 | Kim et al. | |
| 2015/0054917 A1 | 2/2015 | Coon | |
| 2015/0194186 A1 | 7/2015 | Lee et al. | |
| 2015/0253873 A1 | 9/2015 | Sato et al. | |
| 2016/0054802 A1 | 2/2016 | Dickerson et al. | |
| 2016/0062453 A1 | 3/2016 | Quennesson | |

FOREIGN PATENT DOCUMENTS

| | | |
|---|---|---|
| JP | 5340280 | 11/2013 |
| JP | 2014-222445 | 11/2014 |
| KR | 20-0472165 | 4/2014 |
| KR | 10-2014-0081087 | 7/2014 |
| KR | 10-2016-0019741 | 2/2016 |
| WO | WO 2007/000743 | 1/2007 |
| WO | WO 2014/100250 | 6/2014 |

OTHER PUBLICATIONS

PCT/KR2017/005291 Search Report dated Aug. 21, 2017.
Supplemental European Search Report dated Apr. 12, 2019 for EP Application No. 17856544.6.
Extended European Search Report dated Jul. 11, 2019 for EP Application No. 17856544.6.

* cited by examiner

① USER STAND WITH HER BACK FACING DISPLAY FOR CERTAIN PERIOD OF TIME

② USER ROTATE 180°

FIG. 9A
FIG. 9B
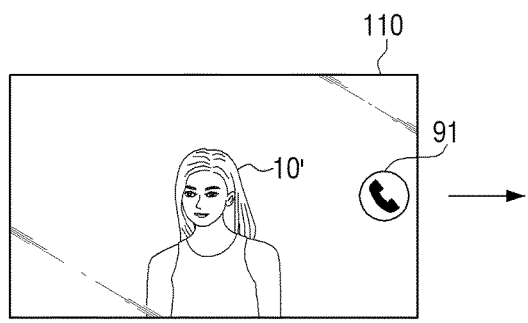
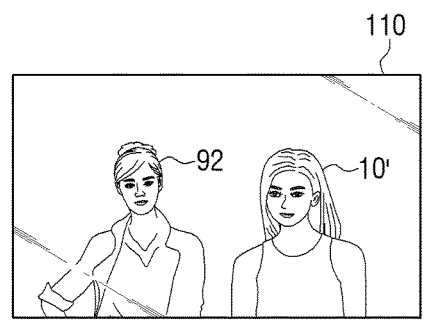
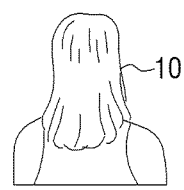
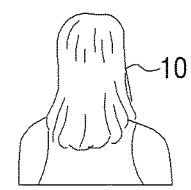

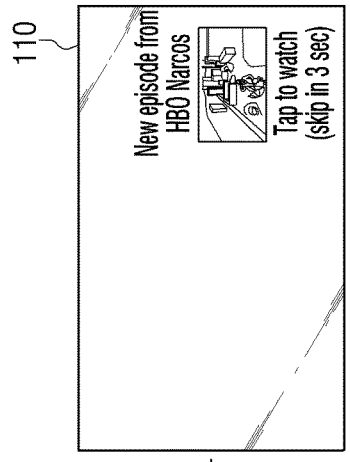
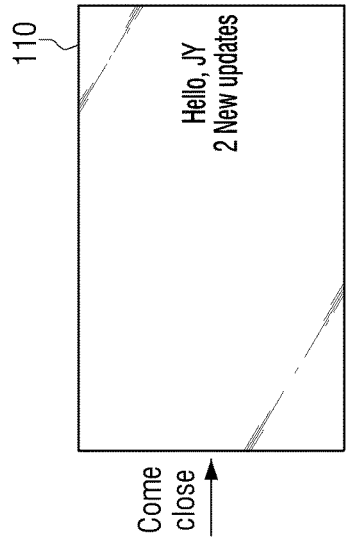
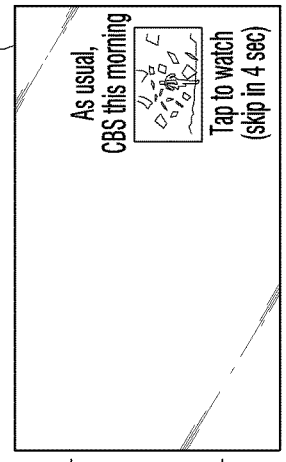
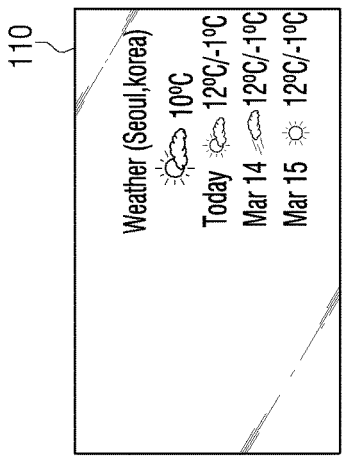
FIG. 12A
FIG. 12B
FIG. 12C
FIG. 12D
FIG. 12E

DISPLAY APPARATUS AND CONTROLLING METHOD THEREOF

CROSS-REFERENCE TO RELATED APPLICATION

This application is based on and claims priority under 35 U.S.C. § 119 to Korean Patent Application No. 10-2016-0125513, filed in the Korean Intellectual Property Office on Sep. 29, 2016, the disclosure of which is incorporated by reference herein in its entirety.

BACKGROUND

1. Field

The present disclosure relates generally to a display apparatus and a controlling method thereof, for example, to a display apparatus which provides various user experiences using a mirror function and a controlling method thereof.

2. Description of Related Art

As a display technology develops, a function of a display apparatus has been extended to include a function considering a decorative aspect of a display apparatus beyond merely providing image information.

In the prior art, in view of a decorative aspect of a display apparatus, a display apparatus has been manufactured to have a slimmer and simpler design than before. Accordingly, a display apparatus has extended its scope of function to work as an item for interior decoration in consideration of a visual aspect of a display apparatus.

Further, a display apparatus can not only display an image, but also can operate in a mirror mode in which a display apparatus works as a mirror while the apparatus is turned off, thereby performing a variety of functions considering not only a visual aspect but also an aspect of a practical use.

Recently, a more user-friendly technology has been required to a display apparatus that can carry out a mirror function beyond a function of merely displaying an image on a display apparatus.

SUMMARY

An aspect of various example embodiments relates to a display apparatus which provides various user experiences using a mirror function and a controlling method thereof.

According to an example embodiment, a display apparatus is provided, the display apparatus including a display configured to operate as at least one of a screen and a mirror, a photographing unit including a camera configured to generate a photographed image in which a subject present in a display direction of the display is photographed, and a processor configured to control the display to operate a first area of the display as a screen displaying part of the photographed image and to operate a second area of the display other than the first area as a mirror.

The processor may, in response to receiving an input gesture selecting a partial area of the subject while the display operates as a mirror, control the display to display part of the photographed image corresponding to the selected partial area on the first area.

The processor may control the display to display an image larger than a mirror image regarding the selected partial area on the first area.

The display apparatus may further include a proximity sensor configured to sense an object within a predetermined proximity to the display, wherein the processor may sense the gesture based on at least one of the photographed image and a sensing result of the proximity sensor.

The processor may detect a plurality of body parts from the photographed image, perform image-processing to highlight at least one of the plurality of detected body parts in the photographed image, and control the display to display the processed image on a first area.

The processor may perform an image-processing of the photographed image to highlight a body part closest to the display among the plurality of detected body parts.

The processor may, in response to determining that a distance between the highlighted body part and the display is equal to or greater than a predetermined distance, control the display to operate the first area of the display as a mirror.

The processor may detect at least two of body parts from among eyes, a nose, a mouth and a head in the photographed image.

The processor may, in response to a gesture of moving the first area out of the display being received, control the display to operate the first area of the display as a mirror.

The processor may generate a capture image of a subject from the photographed image, and control the display to display the generated capture image along with a pre-stored capture image regarding the subject.

The processor may, in response to a back view of a user being sensed, control the display to generate a capture image of the back view of the user, and in response to a front view of the user being sensed, control the display to display the capture image of the back view of the user on the first area.

The processor may, in response to a video call function being performed, sense a position of a user, and based on the sensed position, control the display to display an image of a counterpart of which is received based on the video call function on an area in which a mirror image of the user is not displayed.

Meanwhile, the display apparatus may further include a communicator comprising communication circuitry configured to communicate with an external electronic apparatus, wherein the processor may, in response to a user being detected from the photographed image, control the display to display an identification marker including communication information on an area in which a mirror image of the user is present, and to control the communicator to connect to the electronic apparatus which has photographed the displayed identification marker.

The processor may, in response to a call being received in the electronic apparatus, and the electronic apparatus and the display apparatus being within a predetermined distance, control the display to display a UI element for receiving the call in the display apparatus.

The processor may, in response to a wearable device which collects user health information and stores the information in the electronic apparatus being detected in the photographed image, control the communicator to receive the health information from the electronic apparatus, and control the display to display the received health information.

The processor may identify a user from the photographed image based on pre-stored face information, and control the display to display a content recommendation screen corresponding to the identified user.

The display may include a display panel configured to generate light corresponding to an image and a polarizing film configured to be disposed on a front side of the display panel, transmit light generated in the display panel and reflect light incident from the outside.

Meanwhile, a method for controlling a display apparatus including a display configured to operate as at least one of a screen and a mirror is provided, the method may include generating a photographed image in which a subject present in a display direction of the display is photographed, and controlling the display to operate a first area of the display as a screen displaying part of the photographed image and to operate a second area other than the first area as a mirror.

The controlling may include, in response to receiving an input of a gesture of selecting a partial area of the subject while the display operates as a mirror, controlling the display to display part of the photographed image corresponding to the selected partial area on the first area.

The controlling may include controlling the display to display an image larger than a mirror image regarding the selected partial area on the first area.

BRIEF DESCRIPTION OF THE DRAWINGS

These and other aspects, features and attendant advantages of the present disclosure will become more readily apparent and appreciated from the following detailed description, taken in conjunction with the accompanying drawings, in which like reference numerals refer to like elements, and wherein:

FIGS. 9A and 9B are diagrams illustrating an example video call function of a display apparatus according to an example embodiment of the present disclosure;

FIGS. 12A, 12B, 12C, 12D and 12E are diagrams illustrating an example content recommendation screen displayed on a display apparatus according to an example embodiment of the present disclosure;

DETAILED DESCRIPTION

Figure 1:
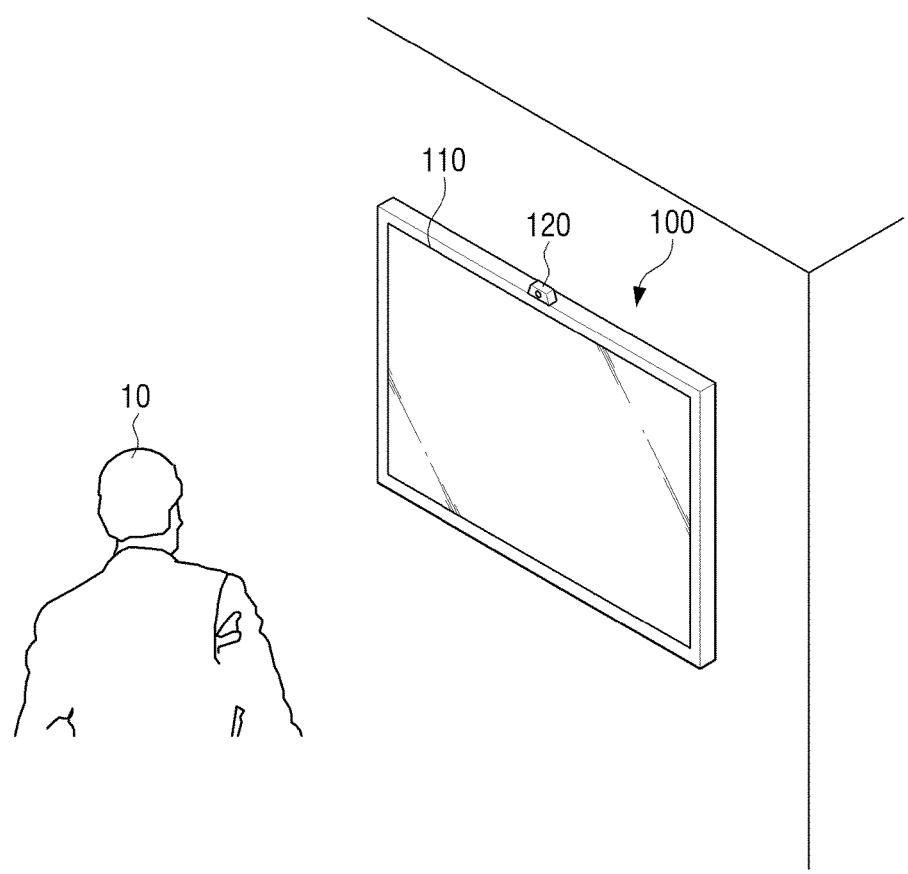
FIG. 1 is a diagram illustrating an example display apparatus according to an example embodiment of the present disclosure.

Hereinafter, various example embodiments of the present disclosure will be described in greater detail with reference to the accompanying drawings.

The terms used in an example embodiment are defined in consideration of a function described in an example embodiment, and the terms may vary according to an intention of a technician practicing in the pertinent art, an advent of new technology, etc. In specific cases, terms may be chosen arbitrarily, and in this case, definitions thereof will be described in the description of the corresponding disclosure. Therefore, the terms used in the description should not necessarily be construed as simple names of the terms, but be defined based on meanings of the terms and overall contents of the present disclosure.

The example embodiments may vary, and may be provided in different example embodiments. Various example embodiments will be described with reference to accompanying drawings. However, this does not necessarily limit the scope of the example embodiments to a specific form. Instead, modifications, equivalents and replacements included in the disclosed concept and technical scope of this description may be employed. Also, well-known functions or constructions may not described in detail if they would obscure the disclosure with unnecessary detail.

The terms such as "first" and "second" may be used to explain various elements, but the elements should not be limited by these terms. The terms are used solely for the purpose of distinguishing one element from another element.

A singular term includes a plural form unless otherwise indicated. It should be understood that the terms "include" or "have" used in the example embodiments of the present disclosure are to indicate the presence of features, numbers, steps, operations, elements, parts, or a combination thereof described in the disclosure, and do not preclude the presence or addition of one or more other features, numbers, steps, operations, elements, parts, or a combination thereof.

In an example embodiment, 'a module' or 'a unit' performs at least one function or operation, and may be realized as hardware, software, or combination thereof. Further, except the "modules" or "units" that have to be implemented as certain hardware, a plurality of "modules" or a plurality of "units" may be integrated into at least one module and realized as at least one processor including various processing circuitry.

Hereinafter, the example embodiments of the present disclosure will be described in greater detail with reference to the accompanying drawings, so that a person skilled in the art can easily understand the example embodiments. However, the example embodiments may be implemented as various different forms, and is not limited to the example embodiments described herein. In the drawings, parts that are not relevant to the description may be omitted to clearly describe the embodiments, and like drawing reference numerals are used for the like elements throughout the disclosure.

Hereinafter, the present disclosure will be described in greater detail with reference to the accompanying drawings.

FIG. 1 is a diagram illustrating an example display apparatus according to an example embodiment of the present disclosure.

Referring to FIG. 1, a display apparatus 100 is configured to display an image. For example, the display apparatus 100 may be implemented by various apparatuses such as a TV, a Tablet PC, a laptop, a desktop, a monitor, a projector or the like, but is not limited thereto. For example, as the display apparatus 100 can perform a mirror function, the display apparatus 100 can be manufactured to be a wall-mounted type.

The display apparatus 100 may include a screen or display 110 and a photographing unit (e.g., including at least one camera) 120. The photographing unit 120 may include various photographing circuitry, such as, for example, and without limitation, a camera that may photograph an object, and generate a still image or a video. The photographing unit 120 may be implemented as a camera in which a lens and an image sensor are provided.

For example, the photographing unit 120 may photograph an object present in the display direction of the display apparatus 100, and generate a photographed image.

The display direction of the display apparatus 100 herein may refer to the direction to the position in which a user who stares at a screen displayed on the display apparatus 100 is present, that is, the front side of the display apparatus 100.

As illustrated in FIG. 1, the photographing unit 120 may be disposed on the upper portion of the display apparatus, but not limited thereto. The photographing unit 120 may also be disposed inside the display apparatus 100, and photograph a user from the front.

The display apparatus 100 according to an example embodiment may be configured to have an image displaying function and a mirror function. Accordingly, the display apparatus 100 may be referred to as 'a mirror display.'

For example, the display apparatus 100 may implement a mirror function by two methods. The first method is, after reversing the right and the left of an image photographed in the photographing unit 200, to display the reversed image. For example, a user 10 is photographed by the photographing unit 120, and if the right and the left of the photographed image are reversed, and the reversed image is displayed, the user may feel as if he or she looks at a mirror when looking at the image.

As the second method, the display apparatus 100 may project a mirror image by reflecting external light. Unlike the first method, light from the user 10 is reflected off the display apparatus 100, and the user 10 can see the reflected light.

In order to implement the second method, for instance, glass may be mounted on the top surface of a display panel of the display apparatus 100. The top surface of the glass may be coated with metal such as aluminum, chrome, titanium or the like. As the external light is reflected off the metal-coated surface, the mirror function can be implemented, and light produced from the display apparatus 100 may be transmitted to the outside of the apparatus. Such the method is referred to as a half-mirror method.

As another example, an electrochromic mirror may be used, the method of which is to electrically convert a mirror state into a transparent state through a redox reaction. For example, a transparent electrode of an electrochromic mirror is provided on the top surface of the display apparatus 100, and on the transparent electrode, an ion storage membrane, an electrolyte membrane, a catalyst layer and an active membrane may be sequentially accumulated. The transparent electrode may be an ITO membrane. The ion storage membrane may store protons required to cause an electrochromic effect. The ion storage membrane may be, for example, a tungsten oxide (WOx) layer. If positive voltage (+) is applied to the transparent electrode of the electrochromic mirror, protons included in the ion storage membrane may move to the upper part of the ion storage membrane, pass the electrolyte membrane and the catalyst layer, and reaches the active membrane. Accordingly, the ion storage membrane and the active membrane may become transparent. Conversely, if negative voltage (−) is applied to the transparent electrode of the electrochromic mirror, the hydrogens that have reached the active membrane may move to the ion storage membrane. As a result, the active membrane may return to an inherent metal property, and the ion storage membrane may become transparent as it turns into a deep blue state again due to protons, that is, the ion storage membrane comes to have a color. In the latter, the display apparatus may operate as a mirror.

As another example, a polarizing film may be disposed on the top surface of the display panel of the display apparatus 100. The polarizing film may include a plurality of polarizing layers that have different refractive indexes to one of vertical polarizing light and horizontal polarizing light, and between vertical polarizing light and horizontal polarizing light, the plurality of polarizing layers may reflect one and transmit the other. Using the polarizing film, the display apparatus 100 may operate as a mirror by reflecting part of light incident from the outside, and simultaneously, a user may see an image by transmitting light produced from the display panel.

Beside the aforementioned examples, the display apparatus 100 may implement a display function and a mirror function using various methods of the prior art.

Further, in the display apparatus 100, not only the whole area of the display apparatus 100 may operate as a mirror, but also only part of the area may operate as a mirror.

Hereinafter, an example configuration of the display apparatus 100 will be described with reference to FIG. 2.

Figure 2:
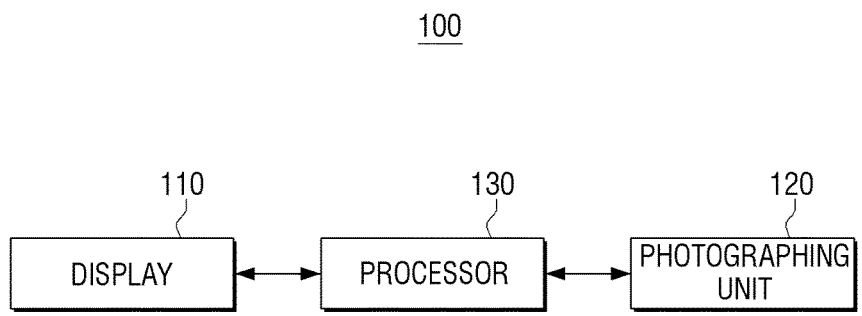
FIG. 2 is a block diagram illustrating an example configuration of a display apparatus according to an example embodiment of the present disclosure.

FIG. 2 is a block diagram illustrating an example configuration of the display apparatus 100 according to an example embodiment of the present disclosure. The display apparatus 100 may include the display 110, the photographing unit 120 and the processor (e.g., including processing circuitry) 130.

The display 110 may refer, for example, to a component to display various screens. The display 110 may be, for example, implemented as a cathode-ray tube (CRT), a plasma display panel (PDP), an organic light emitting diodes (OLED), a transparent OLED (TOLED) or the like, but is not limited thereto. The display may also be implemented as a touch screen which can sense a touch manipulation of a user.

Figure 3:
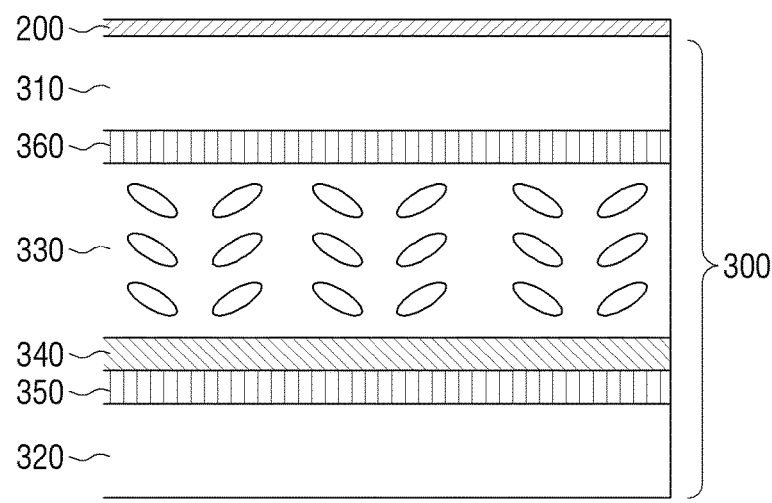
FIG. 3 is a diagram illustrating an example display of a display apparatus according to an example embodiment of the present disclosure.

Referring to FIG. 3, an example in which the display apparatus 100 is implemented as an apparatus which can carry out a mirror function by the aforementioned second method.

FIG. 3 illustrates the display 110 according to an example embodiment of the present disclosure.

Referring to FIG. 3, light irradiated in Z direction from a backlight unit (not illustrated) may be incident to the display panel 300, and be emitted in Z direction passing through the components of the display panel 300. Hereinafter, the expressions of an upper portion/an upper side and a lower portion/a lower side are to indicate a relative arrangement or an accumulation relationship constructed according to Z direction which is a movement direction of the irradiated light.

The display panel 300 may include an upper substrate 310, a lower substrate 320 configured to be disposed facing the upper substrate 310, a liquid crystal layer 330 configured to be disposed between the upper substrate 301 and the lower substrate 320, a color filter layer 340 configured to be inserted between the liquid crystal layer 330 and the lower substrate 320, a lower polarizing layer 350 configured to be disposed on the upper side of the lower substrate 320, and a upper polarizing layer 360 configured to be disposed on the lower side of the upper substrate 310.

The upper substrate 301 and the lower substrate 320 may be transparent substrates disposed facing each other with a certain gap according to movement of light. Different characteristics may be required from the upper substrate 310 and the lower substrate 320 according to an operation method of the liquid crystal layer 330. For example, if an operation method of the liquid crystal layer 330 is a passive matrix, soda lime glass may be used, and if the liquid crystal layer 330 is an active matrix, alkali free glass and borosilicate glass may be used.

The liquid crystal layer 330 may be sandwiched between the upper substrate 301 and the lower substrate 320, and regulate light transmission by changing an arrangement of liquid crystals based on a supplied operation signal. Once power is supplied to the liquid crystal, an arrangement of molecules is changed, and the optical property is also changed accordingly. In case of liquid crystal of the liquid crystal layer 330, there are four types of liquid crystal: nematic liquid crystal, cholesteric liquid crystal, smectic liquid crystal and ferroelectric liquid crystal.

The color filter layer 340 may be disposed between the liquid crystal layer 330 and the lower substrate 320, and filter incident light in order for light of a certain color to each pixel of the liquid crystal layer 330 to be emitted.

The color filter layer 340 may convert light incident to the display panel 100 into RGB colors, and transfer the colors to the liquid crystal layer 330. The pixels of the liquid crystal layer 330 may include sub-pixels corresponding to each of RGB colors, and the color filter layer 340 may filter each color according to each sub-pixel. Accordingly, when light passes through each sub-pixel, different colors and beams of light may be emitted from each sub-pixel by the color filter layer 340. In the example embodiment, it is described that the color filter layer 340 may be disposed in the lower substrate 320, but the position of the color filter layer 340 may not be limited thereto. The color filter layer 340 may be disposed in the upper substrate 301.

The lower polarizing layer 350 may be disposed between the lower substrate 320 and the color filter layer 340, and the upper polarizing layer 360 may be disposed between the upper substrate 310 and the liquid crystal layer 330. The lower polarizing layer 350 and upper polarizing layer 360 may be configured to transmit incident light of pre-determined polarization direction. Each polarization direction of light transmitted by the lower polarizing layer 350 and upper polarizing layer 360 may be identical or different according to a designed method.

In addition, as illustrated in FIG. 3, a mirror 200 may be disposed on the surface of the upper plate of the display panel 300.

According to an example embodiment, the mirror 200 may be a polarizing film. The polarizing film, that is the mirror 200, may transmit light produced in the display panel 300, and provide a display image to a user, and also project a mirror image by reflecting part of external light.

According to another example embodiment, the mirror 200 may be an electrochromic mirror. The electrochromic mirror may operate in a penetration (transparent) mode and a reflection (mirror) mode according to a voltage property of supplied power.

According to another example embodiment, the mirror 200 may be a half mirror (or a translucent mirror or a one-way mirror).

If the electrochromic mirror is disposed on the top surface of the display 110, the electrochromic mirror may operate in a penetration (transparent) mode and a reflection (mirror) mode based on a voltage property of supplied power. In the penetration mode, the electrochromic mirror may operate as a screen, and in the reflection mode, it may operate as a mirror.

According to another example embodiment, the display 110 may operate as a screen and simultaneously operate as a mirror. For example, in the case where a polarizing film or a half mirror is disposed on the top surface of the display 110, as light of a backlight unit can be transmitted and also external light can be reflected, the display 110 may display a screen, and simultaneously operate as a mirror.

The photographing unit 120 may be an apparatus which photographs a subject, and generates a still image or a video. The photographing unit 120 may, for example, be implemented as a camera. The photographing unit 120 may be provided inside the display apparatus 100, or be provided as a separate apparatus which can connect with the display apparatus 100 via cable or wirelessly.

The photographing unit 120 may generate a photographed image in which a subject present in a display direction of the display is photographed. The image herein may include a video and a still image.

The processor 130 may include various processing circuitry and control overall operations of the display apparatus 100. The processor 130 may include a CPU, a RAM, a ROM and a system bus. In the foregoing example embodiment, it is described that the processor 130 may include various processing circuitry, such as, for example one CPU, but the processor 130 may also be implemented by a plurality of CPUs (or DSP, MPU, etc.), a dedicated processor, or the like. Further, the processor 130 may be implemented as a micro-computer (MICOM), application specific integrated circuit (ASIC), or the like, but is not limited thereof.

The processor 130 may control the display in order for a first area of the display 110 to operate as a screen displaying part of an image photographed by the photographing unit 120, and a second area other than the first area to operate as a mirror. Referring to FIG. 1, a user may see a photographed image of himself/herself on the first area, and on the second area, the user may see a mirror image, that is, the reflection of himself/herself.

The processor 130 may, in response to a gesture of selecting a partial area of the subject being input while the display operates as a mirror, control the display 110 to display, within an image photographed by the photographing unit 120, part of the photographed image corresponding to the selected partial area on the first area, and control the display 110 in order for the second area other than the first area to operate as a mirror. This will be described in greater detail below with reference to FIGS. 4A, 4B and 4C.

Figure 4A:
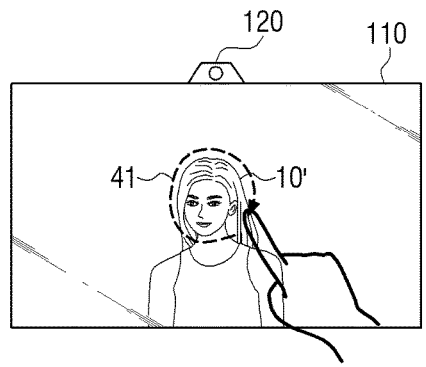
FIGS. 4A, 4B, 4C, 5A, 5B and 5C are diagrams illustrating various example embodiments of the present disclosure in which a display apparatus displays a mirror image along with a photographed image.
Figure 4A:
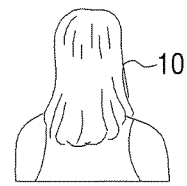

Referring to FIG. 4A, a mirror image 10' is displayed, the image which is created by light from the subject 10 being reflected off the display 110 while the display 110 operates as a mirror, and the gesture of selecting a partial area 41 of the subject may be input. In FIG. 4A, a hand is illustrated separately in order to explain the gesture, but the hand is of the subject 10.

The gesture of selection the partial area 41 of the subject may be input by various methods.

According to an example embodiment, if the movement of the user hand included in the image photographed by the photographing unit 120 is a movement of pointing at a certain part of the display, or of drawing a circle on a certain part, the processor may determine that the gesture of selecting the subject being displayed on the certain part has been input. The gesture does not have to be of gesturing towards the display 110, but the gesture such as directly pointing at a certain part of the subject (e.g., touching an eye with a finger) is sensed, the processor 130 may determine that the gesture of selecting the certain part of the subject has been input.

According to another example embodiment, the display apparatus 100 may include a proximity sensor (e.g., an IR proximity sensor), and sense an object in proximity (e.g., a predetermined proximity) to the display 110. Also, a user gesture may be determined by the proximity sensor.

As described above, not only a gesture that a user does not contact with the display 110, but the gesture of contacting with the display 110 may also be sensed. For example, the display 110 may be implemented as a touch panel, and when it is sensed that a user touches a certain part of the display 110, or a user touches a certain part and draws a circle in the certain part, the processor 130 may determine that a gesture of selecting a subject displayed on the certain part has been input.

Figure 4B:
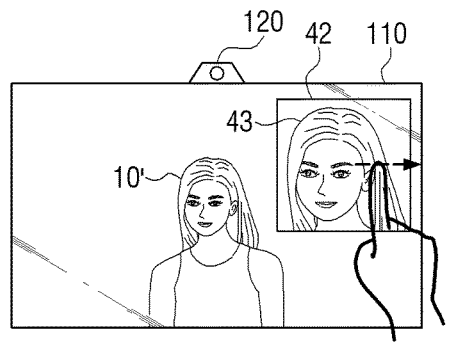
Figure 4B:
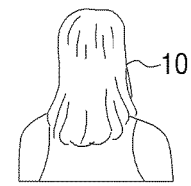

Referring to FIG. 4B, the processor 130 may display, on the first area 42 operating as a screen, a partial area of a photographed image 43 which corresponds to the partial area 41 selected from a subject, and control the display 110 in order for the area other than the first area to operate as a mirror.

In the foregoing example, the processor 130 may control the display 110 in order for an image 43 larger than a reflected image (or a mirror image) corresponding to the partial area 41 selected from a subject to be displayed on the first area 42. Accordingly, the user 10 may see, on the first area 42, an image of his/her face enlarged from the image of his/her face seen on the mirror.

Figure 4C:
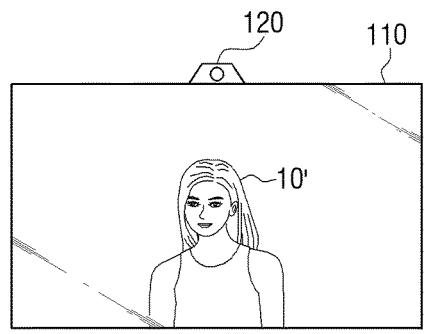
Figure 4C:
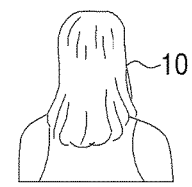

Further, the processor 130 may, in response to a predetermined user gesture being input, control the display 110 in order for the first area 42 to operate as a mirror area. That is, the processor 130 may, in response to a predetermined user gesture being input, control the display 110 in order for the image 43 not to be displayed anymore. According to an example embodiment, as illustrated in FIG. 4C, the processor 130 may, in response to an input of a gesture of moving the first area 42 on which the image 43 is displayed out of the display 42, control the display 110 in order for the first area 42 to operate as a mirror. That is, as the processor 130 may control the display 110 not to display any image on the first area 43, the display 110 may operate as a mirror.

The processor 130 may detect a plurality of body parts from an image photographed by the photographing unit 110, performs an image processing to highlight at least one of the detected body parts in the photographed image, and control the display 110 to display the processed image.

According to an example embodiment, the processor 130 may detect a face area by recognizing eyes, a nose and a mouth which are feature areas on the photographed image, and may also detect a head, an arm, a leg, etc. based on a pre-stored image (e.g., a pre-stored skeleton image).

The processor 130 may highlight at least one of a plurality of detected body parts by differentiating the color of the body part from the colors of the other body parts, draw an edge of the body part or enlarge the body part, and display the image.

The above-described operations may be carried out if it is determined that a user approaches the display 100. It will be described with reference to FIGS. 5A, 5B and 5C.

Figure 5A:
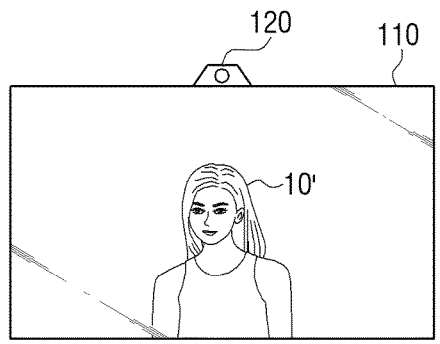
Figure 5A:
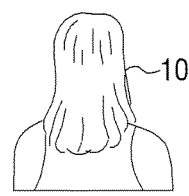
Figure 5B:
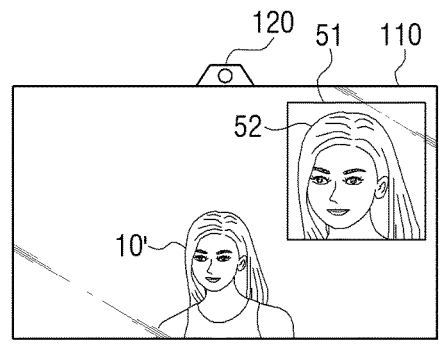
Figure 5B:
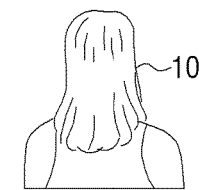

Referring to FIG. 5A, the user 10 is standing looking at the display 110 operating as a mirror, and on the display 110, a mirror image 10' is displayed on the display 110, the image which is created by light from the user being reflected off the display 110. FIG. 5B illustrates the situation in which the user 10 comes even closer to the display 110. The processor 130 may calculate (e.g., determine) the distance between the user 10 and the display 100 through an image photographed by a photographing unit 120 or the proximity sensor. If it is determined that the distance is equal to or less than the predetermined distance, the processor 130 may detect a plurality of predetermined body parts from the photographed image.

The body parts, which are detected objects, may include at least two of eyes, a nose, a mouth and a face. In addition, the processor may perform an image-processing to highlight a certain body part, and display the processed image on the first area 51. For example, the processor 130 may control the display 110 to display an enlarged head image 52 as illustrated in FIG. 5B.

Figure 5C:
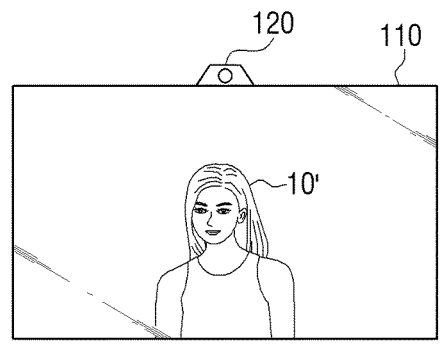
Figure 5C:
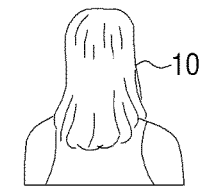

Then, if it is determined that the distance between the body part corresponding to an image displayed on the first area 51 and the display 110 is equal to or greater than a predetermined distance, as illustrated in FIG. 5C, the processor 130 may control the display 110 in order for the first area 51 to operate as a mirror. That is, as the processor 130 may control the display 110 not to display any image on the first area 51, the display 110 may operate as a mirror.

Also, if it is determined that the distance between the body part corresponding to the image displayed on the first area 51 and the display 110 is equal to or greater than a predetermined distance, the processor 130 may not immediately stop displaying the head image 51, but stop the displaying the head image after maintaining the displaying for a certain period of time.

In the foregoing example, it is described that a plurality of body parts may be detected, but it is also possible to detect only one body part that a user wants to highlight.

Figure 6A:
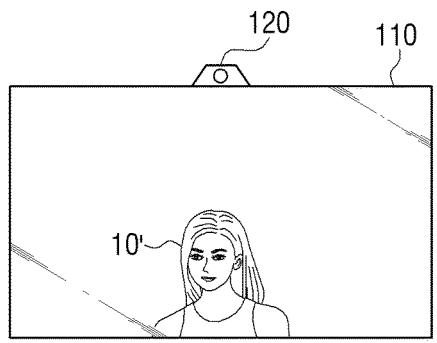
FIGS. 6A, 6B and 6C are diagrams illustrating an example magnifying function of a display apparatus according to an example embodiment of the present disclosure.
Figure 6A:
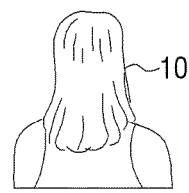
Figure 6B:
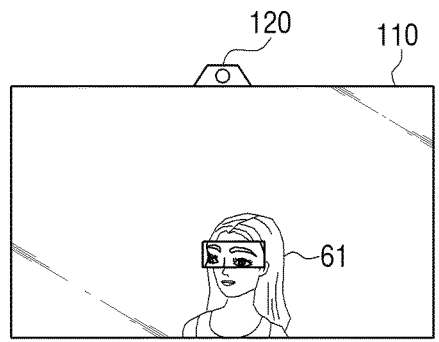
Figure 6B:
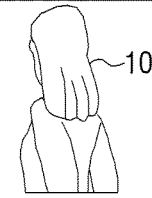
Figure 6C:
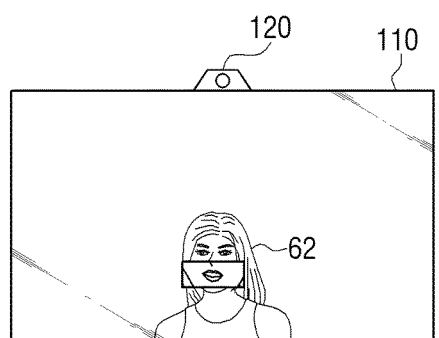
Figure 6C:
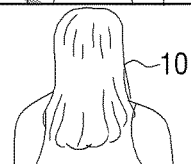

FIGS. 6A, 6B and 6C are diagrams illustrating another example embodiment of the present disclosure with respect to displaying a body part of a user in a photographed image.

Referring to FIG. 6A, a user 10 is standing looking at the display which operates as a mirror, and on the display 110, a mirror image 10' is displayed on the display 110, the image which is created by light from the user 10 being reflected. FIG. 6B illustrates an example in which the user 10 comes even closer to display 110. The processor 130 may calculate (e.g., determine) the distance between the user 10 and the display 100 through an image photographed by a photographing unit 120 or the proximity sensor. If it is determined that the distance is equal to or less than the predetermined distance, the processor 130 may detect a plurality of predetermined body parts from the photographed image. The body parts, which are detected objects, may include eyes, a nose, a mouth and a face.

In addition, the processor 130 may perform an image-processing a photographed image to highlight the body part which is the closest to the display 110, and control the display 110 to display the processed image. FIG. 6B illustrates an example in which the closest body parts are eyes among eyes, a nose and a mouth. The processor 130 may control the display 110 to display the processed image 61 in which the size of the eyes have been enlarged.

According to an example embodiment, the body part which is closest to the display 110 may be determined by the method as below. The processor 130 may measure each size of eyes, a nose and a mouth detected from a photographed image, compare the detected sizes with pre-stored information on the eyes, nose and mouth according to the distance, and determine the body part that is the closest to the display 110 among the detected eyes, nose and mouth. Further, the processor 130 may measure the distance between the eyes, compare the measured distance with pre-stored information on the distance between the eyes according to the head direction, and determine which of the eyes are even closer to the display 110. Also, the processor may identify the degree of a face by detecting the position and the shape of a certain body part (e.g., ears) from a photographed image.

The processor may analyze a photographed image in real time, and automatically highlight the body part which has become close. If the eyes of the user 10 are positioned closest to the display 110 as in FIG. 6B, and then the mouth of the user 10 is positioned far closer to the display than the eyes as illustrated in FIG. 6C, the processor 130 may control the display 110 to display the processed image 62 in order to enlarge the mouth instead of the eyes.

Figure 7A:
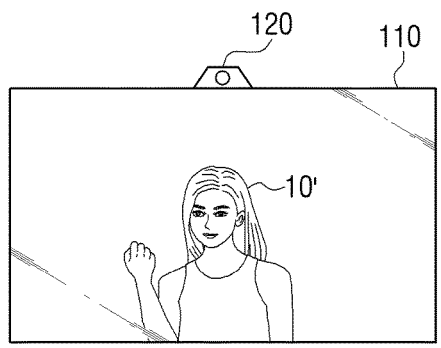
FIGS. 7A, 7B and 7C are diagrams illustrating an example embodiment of the present disclosure in which a currently captured image and a formerly captured image are displayed together in a display apparatus.
Figure 7A:
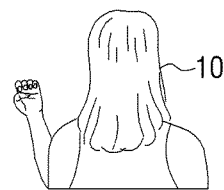
Figure 7B:
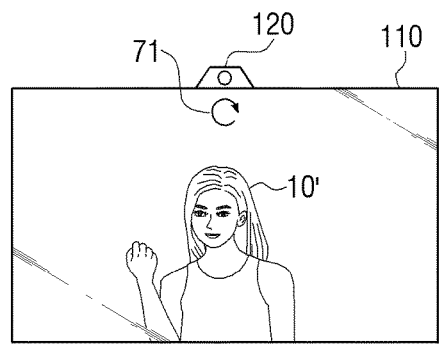
Figure 7B:
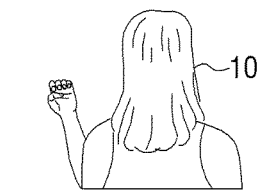
Figure 7C:
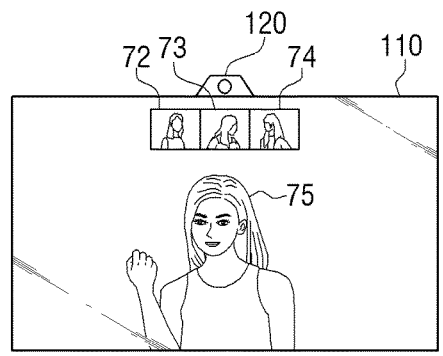
Figure 7C:
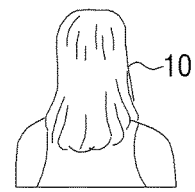

FIGS. 7A, 7B and 7C are diagrams illustrating an example capture image display in the display apparatus 100 according to an example embodiment of the present disclosure.

The processor may, in response to a predetermined gesture being sensed, generate a capture image from a photographed image in which a subject is photographed. The capture image may be a picture. The detecting of a predetermined gesture may be performed when a user, a subject, stands in front of the display 110 for a certain period of time, or a user strikes a certain pose in front of the display. In another example embodiment, the processor 130 may generate a capture image from a photographed image at every predetermined time. For example, at two PM every day, a capture image of a subject positioned in front of the display 110 may be generated.

FIG. 7A illustrates an example in which the user 10 is standing for a certain period of time looking at the display 110 which operates as a mirror. The processor 130 may, if it is detected that the user has been standing in front of the display 110 for a certain period of time, control the photographing unit 120 to generate a capture image from a photographed image. In this case, a UI element 71 which notifies that photographing is soon performed as illustrated in FIG. 7B.

Once the photographing is completed, a currently captured image 75 may be displayed on the display 110 as illustrated in FIG. 7C. In this case, pre-stored capture images of a user, the capture images 72, 73 and 74 which were photographed by a user in front of the display 110 in the past, may also be displayed together.

As described above, the display apparatus 100 may include a storage which can store capture images. The storage may be implemented as a non-volatile memory, a volatile memory, a flash memory, a hard disk drive (HDD), a solid state drive (SSD), or the like, but is not limited thereto. The storage 110 may be accessed by the processor 130, and reading/recording/editing/deleting/updating of data may be carried out by the processor 130. Also, the storage 110 may be implemented not only as a storage medium inside the display apparatus 100 but also as an external storage medium such as a USB, a web server through network or the like. In the storage, a program such as an operating system (OS) or various applications, user set data, data generated while an application is performed, various data such as multimedia contents, etc. may be stored.

Figure 8A:
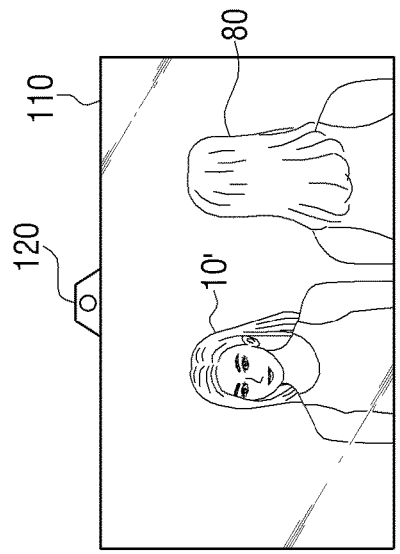
FIGS. 8A and 8B are diagrams illustrating an example embodiment of the present disclosure in which a front appearance and a back appearance may be checked simultaneously.
Figure 8A:
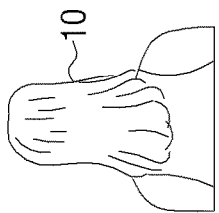
Figure 8B:
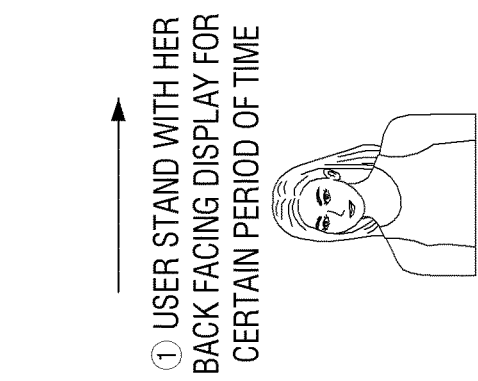
Figure 8B:
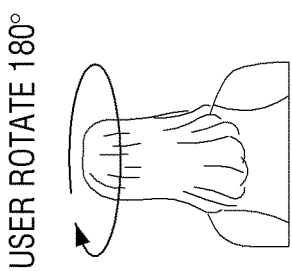
Figure 8B:
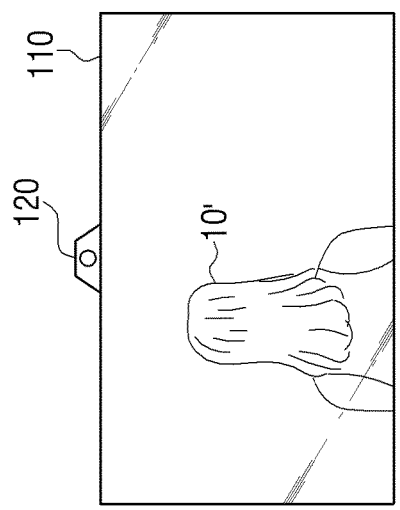
Figure 8B:
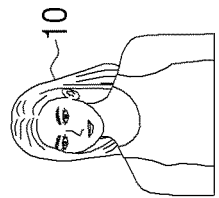

FIGS. 8A and 8B are diagrams illustrating an example embodiment of the present disclosure with respect to photographing a back view of a user.

FIG. 8A illustrates an example in which the user 10 is standing with her back facing the display 110 which operates as a mirror. The processor 130 may, in response to the back view of a user in an image photographed by the photographing unit 120 being sensed, generate a capture image of the back view of the user from the photographed image.

The processor 130 may, if a shape corresponding the pre-stored shape of a human back is detected for equal to or longer than a predetermined time period, determine that the back view of the user is sensed.

Then, the processor 130 may, if the front view of the user is sensed, that is, if a face, etc. is sensed from the photographed image, for example, the capture image 80 of the back view of the user which has been previously generated may be displayed as illustrated in FIG. 8B. In this case, the capture image 80 of the back view of the user 10 may be displayed on the area other than the area in which the mirror image 10' of the user 10 is present. The processor 130 may, based on the proximity sensor and a photographed image, identify the position of the user 10 when the reference point is the display 110, and on the basis of the position, the processor 130 may identify the area in which the mirror image 10' of the user 10 is present.

According to the aforementioned example embodiment, the mirror image 10' to which the front view of the user is projected and the capture image 80 of the back view may be simultaneously displayed.

FIGS. 9A and 9B are diagrams illustrating an example embodiment of the present disclosure with respect to a video call.

Referring to FIGS. 9A and 9B, the display apparatus 100 may perform a video call function. As illustrated in FIG. 9A, the display apparatus 100 may, in response to receiving a video call request from the outside, control the display 120 to display a UI element 91 for commencing a video call.

If the UI element 91 for commencing a video call is selected, the processor 130 may display an image 92 of a counterpart of a received call on the display 110 according to the video call function as illustrated in FIG. 9B. In this case, the processor 130 may sense the position of a user based on the proximity sensor or a photographed image, and based on the sense position, the processor 130 may control the display 110 to display the image 92 of the counterpart on the area in which the mirror image 10' of the user 10 is not displayed. For example, the user may carry out a video call while she sees the reflection of herself on the area operating as a mirror, and sees the counterpart displayed on the other area. Accordingly, the user may feel as if she is in the same space with the counterpart.

The display apparatus 100 may further include a communicator which communicates with an external apparatus. The communicator may include various communication circuitry which communicates with various types of external apparatuses according to a variety of communication methods. The communicator may include a variety of communication circuitry in the form of communication chips, such as, for example, and without limitation, a Wi-Fi chip, a Bluetooth chip, an NFC chip, a wireless communication chip, or the like. A Wi-Fi chip, a Bluetooth chip and an NFC chip may communicate by methods of Wi-Fi, Wi-Fi-direct, Bluetooth and NFC, respectively. The NFC chip refers to a communication chip that operates by an NFC method that uses a 13.56 MHz band among various RF-ID frequency bands such as 135 kHz, 13.56 MHz, 433 MHz, 860~960 MHz and 2.45 GHz. In case of using a Wi-Fi chip or a Bluetooth chip, various connection information such as a SSID, a session key, etc. may be firstly transmitted and received, communication connection is carried out, and then various information may be transmitted and received. The wireless communication chip refers to a communication chip which communicates according to various communication standards such as IEEE, ZigBee, 3rd Generation (3G), 3rd Generation Partnership (3GP), Long Term Evolution (LTE), or the like.

FIGS. 10A, 10B, 10C and 10D are diagrams illustrating an example embodiment of the present disclosure illustrating connecting an external electronic apparatus and the display apparatus 100.

Figure 10A:
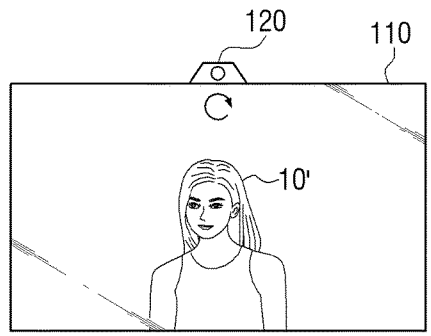
FIGS. 10A, 10B, 10C and 10D are diagrams illustrating an example connection between a display apparatus and an external apparatus according to an example embodiment of the present disclosure.

FIG. 10A illustrates an example in which the user 10 is standing looking at the display 110 operating as a mirror. On the display 110, the mirror image 10' may be displayed, the image which is formed by light from a user being reflected. The processor 130 may, in response a user being detected from an image photographed by the photographing unit 120, identify the detected user based on pre-stored face information. If there is no information matched to a face of the user 10 in the pre-stored face information, the processor may determine that the user is a new user.

If it is determined that the user is a new user, the processor 130 may generate an identification marker including connection information using the user shape (or an outline and a silhouette) detected from the photographed image. Also, the processor 130 may store the user face in the photographed image, and when the user is photographed again later, the processor 130 may analyze the user face and use the analysis as data for logging-in.

Figure 10B:
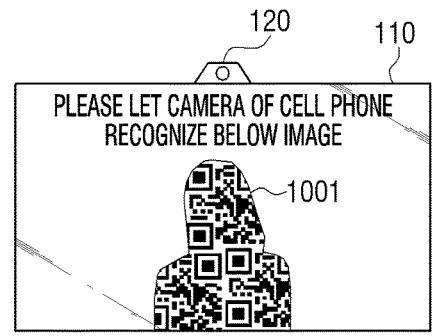
Figure 10B:
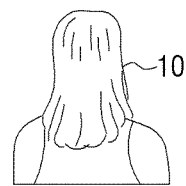

The processor 130 may control the display 110 to display the identification marker 1001 on the area in which the mirror image 10' of the user is present as illustrated in FIG. 10B. The processor 130 may identify the area in which the mirror image 10' is present based on the position of a user in the photographed image and the position of the photographing unit 120 in the display apparatus 100.

The identification marker may be a machine-readable marker such as a QR code and a bar code, or the like, but is not limited thereto.

Figure 10D:
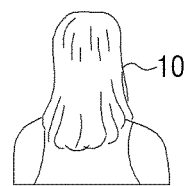
Figure 10C:
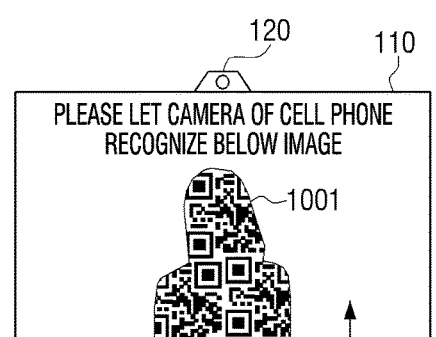
Figure 10C:
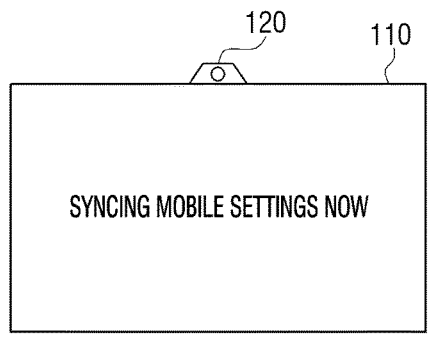
Figure 10C:
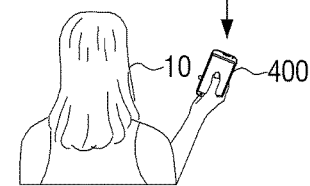

Referring to FIG. 10C, the identification marker 1001 may be photographed using the electronic apparatus 400 such as a smartphone, and connection information may be collected. The connection information may be information for connecting with the display apparatus 100 by a wireless communication method. In the case of the wireless communication method such as WI-FI, Bluetooth, etc., information on a session key may be included in connection information. The connection information may also include information on an ID of the display apparatus 100, functions supportable in the display apparatus 100 and the like.

The processor 130 may control the communicator of the display apparatus 100 to connect with the electronic apparatus which has photographed the identification marker 1001.

Once the connection with the electronic apparatus 400 is established, the processor 130 may sync various settings of the electronic apparatus 400 with the display apparatus 100, and display the screen of FIG. 10D.

For example, the processor 130 may sync information such as an ID and a password of an account (e.g., a Facebook™ account, a Google™ account, a Tweeter™ account, etc.) stored in the electronic apparatus 400.

Also, the processor 130 may sync information set through an application such as a mirror manager installed in the electronic apparatus 400. The mirror manager App may provide a function that a user can select and store information (e.g., time, weather, a personal call history, an itinerary, health information, news, etc.) which the user needs.

If a user is photographed later and the face of the user is recognized, the processor 130 may reflect the stored account information, settings, and the like.

Figure 11A:
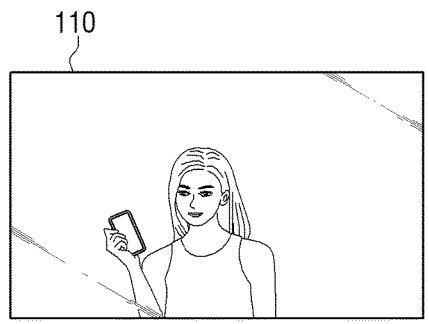
FIGS. 11A, 11B and 11C are diagrams illustrating an example embodiment of the present disclosure in which a display apparatus picks up a call of an external electronic apparatus.
Figure 11A:
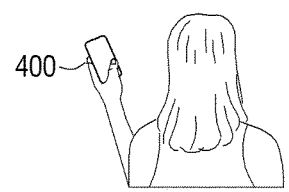
Figure 11B:
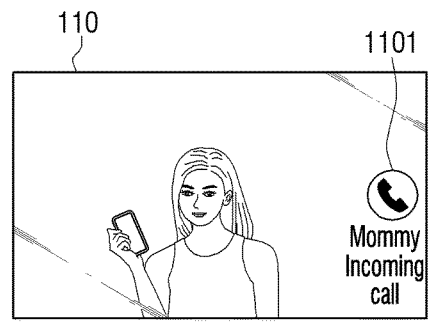
Figure 11B:
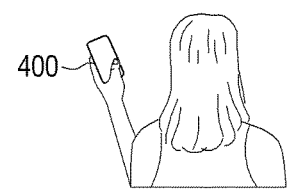
Figure 11C:
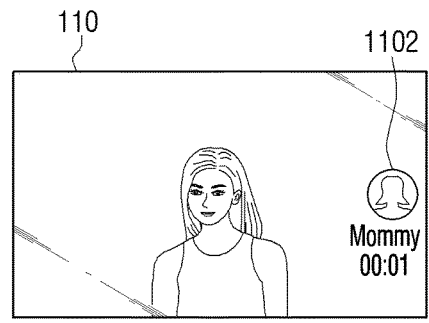
Figure 11C:
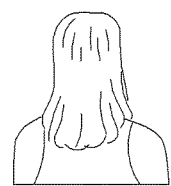

FIGS. 11A, 11B and 11C are diagrams illustrating an example embodiment of the present disclosure illustrating receiving, in a display apparatus, a call received in an external electronic apparatus.

As a microphone and a speaker are provided inside the display apparatus 100, and the display apparatus 100 and the electronic apparatus 400 (e.g., a smartphone) may communicate with each other, a call received in the electronic apparatus 400 may be received in the display apparatus. For example, if a call is received in the electronic apparatus 400 of a user, the electronic apparatus 400 may transmit information which notifies that a call is received in the electronic apparatus 400 to the display apparatus 100. Such the information may be controlled to be transmitted only when the distance between the display apparatus 100 and the electronic apparatus 400 of the user is within a predetermined distance. In this case, various communication methods such as Bluetooth, Wi-Fi, NFC, etc. may be used.

Referring to FIG. 11A, the diagram illustrates a situation in which, when a call is received in the electronic apparatus 400, the electronic apparatus 400 of a user and the display apparatus 10 are apart from each other by a certain distance or more than a certain distance. Also, FIG. 11B illustrates a situation in which the distance between the electronic apparatus 400 and the display apparatus 100 is equal to or less than a predetermined distance. The processor 130 may measure the distance between the electronic apparatus 400 and the display apparatus 100 based, for example, on the strength of a signal received from the electronic apparatus 400, and if it is determined that the distance is equal to or less than a predetermined distance, the processor 130 may receive information of a person who called. Then, as illustrated in FIG. 11B, a UI element 1101 for receiving a call including the information of a person who called may be displayed. In response to the UI element 1101 for receiving a call being selected, the call received in the electronic apparatus 400 may be picked up in the display apparatus 100. FIG. 11C illustrates a state in which a call has been picked up and received in the display apparatus 100, and a UI element 1102 which notifies that the user is being connected to the person who called may be displayed on the display 110.

According to an example embodiment, a user may, for example, comfortably speak on the phone while the user is applying make-up in front of the display apparatus 100 without holding a cell phone.

FIGS. 12A, 12B, 12C, 12D and 12E are diagrams illustrating an example embodiment of the present disclosure with respect to provision of a recommended content.

Referring to FIGS. 12A and 12B, when a user approaches the display apparatus 100, the processor 130 may identify the user.

The processor 130 may identify a user present in front of the display 110 by operating the photographing unit 120 when a person is sensed through an IR proximity sensor provided inside the display apparatus 100, or by recognizing a voice through a microphone provided inside the display apparatus 100. Or the processor 130 may identify a user from an image photographed by the photographing unit 120 based on pre-stored face information.

The processor 130 may control the display 110 to display information corresponding to the identified user as illustrated in FIG. 12B. Also, the processor 130 may control the display 110 to display a content recommendation screen corresponding to the identified user as illustrated in FIG. 12C. For example, the content recommendation screen may be displayed based on an age of the identified user, viewing information, a viewing pattern stored with regard to the identified user, and the like. The screen of FIG. 12C may be displayed after a predetermined time is elapsed after the screen of FIG. 12B is displayed.

When a user selects a recommended content on the screen of FIG. 12C, the processor 130 may control the display 110 to reproduce the selected content. If the selection of a content is not carried out for a certain period of time on the screen of FIG. 12C, the processor 130 may control the display 110 to display a content recommendation screen including another content as in the screen of FIG. 12D. If the recommended content is selected, the selected recommended content is reproduced, and if the selection is not carried out within a predetermined time period, the processor 130 may control the display 110 to display a basic screen including weather information as in FIG. 12E.

Figure 13:
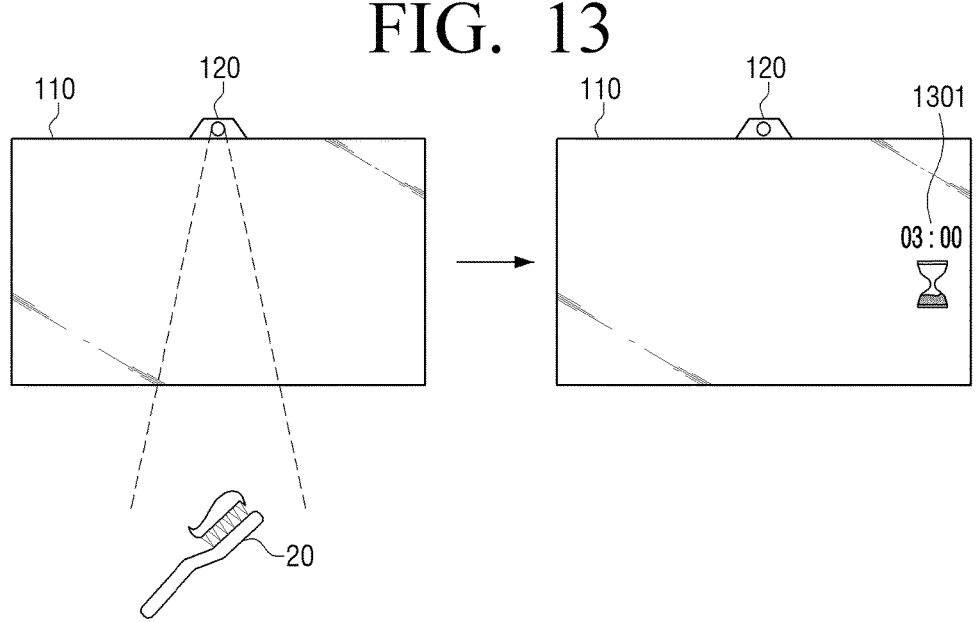
FIG. 13 is a diagram illustrating an example embodiment of the present disclosure with respect to performing a function corresponding an object detected from a photographed image.

FIG. 13 is a diagram illustrating an example embodiment of the present disclosure illustrating providing information associated with a recognized object.

Referring to FIG. 13, the processor 130 may, if a certain object is recognized in an image photographed by the photographing unit 120, for example, if a toothbrush is recognized, control the display to display a timer 1301. Based on the timer 1301, the user may brush his/her teeth for the recommended time, three minutes.

The processor 130 may, if a wearable device which collects user health information from the image photographed by the photographing unit 120 and stores the collected information in the electronic apparatus 400 is detected, control the communicator to receive health information from the electronic apparatus 400 of the user, and control the display 110 to display the received health information. The wearable device herein may be a smart watch, and the health information may be information such as a body weight and walking information.

According to another example embodiment, the display apparatus 100 may provide a function of doodling on a face. For example, the processor 130 may reverse the right and the left of an image in which a user is photographed, and display the image on the display 110. Then, the processor 130 may sense a gesture of a user, and input, on the displayed image, a picture or a doodling based on the gesture of the user. Then, the processor 130 generate a composite image by combining the input picture or a doodling with the photographed image whose the right and the left have been reversed, and store the composite image.

Meanwhile, in the above-described example embodiments, it is assumed that the display apparatus 100 is equipped with a polarizing film, a half mirror or the like, and it is described that a mirror image may be displayed as light that is incident to the display apparatus 100 from the outside is reflected. However, various example embodiments may also be applied when the display apparatus 100 is not equipped with a polarizing film, a half mirror, or the like. For example, a mirror image may be produced by reversing the right and the left of an image photographed by the photographing unit 120. Further, in the various example embodiments described above, it is described that, by displaying no image on a certain area of the display 110, the certain area may operate as a mirror. However, if a mirror image is generated using the photographing unit 120, an image which is currently photographed by the photographing unit 110 may be displayed after reversing the right and the light of the image in order to operate a certain area of the display 110 to operate as a mirror.

Figure 14:
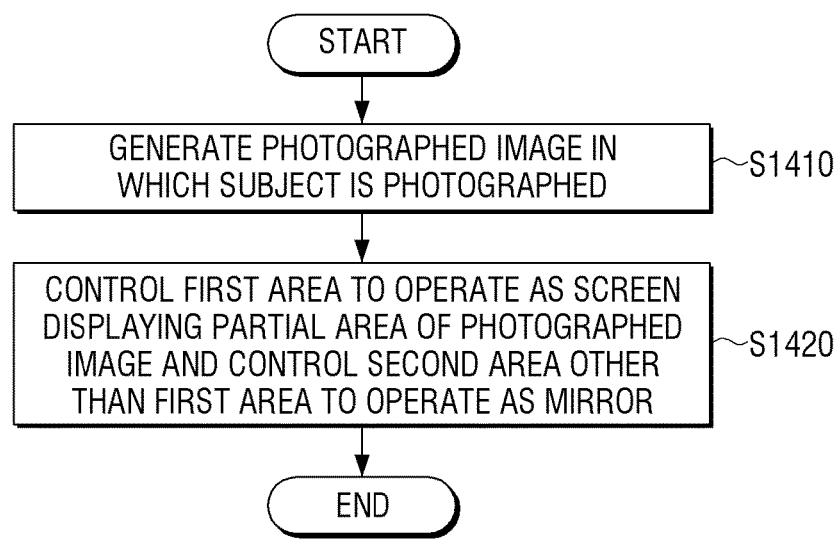
FIG. 14 is a flowchart illustrating an example method for controlling a display apparatus according to an example embodiment of the present disclosure.

FIG. 14 is a flowchart illustrating an example method for controlling the display apparatus 100 including a display operating as at least one of a screen and a mirror according to an example embodiment of the present disclosure.

The display apparatus 100 may generate an image in which a subject present in a display direction of a display is photographed (S1410).

The display apparatus 100 may control the display in order for a first area of the display to operate as a screen displaying part of the photographed image and a second area other than the first area to operate as a mirror (S1420).

To control the display to operate as a mirror may, if the display apparatus 100 is equipped with a component such as a polarizing film that can reflect external light, control the display not to display an image. If the display 100 is not equipped with such the component, it may reverse the right and the left of an image in which the situation in front of the display apparatus 100 is photographed and to display the image on the display in real time.

Meanwhile, the display apparatus 100 may, in response to a gesture of selecting a partial area of the subject while the display operates as a mirror, control the display to display part of the photographed image corresponding to the selected partial area on the first area.

The display apparatus 100 may further include a proximity sensor which senses an object in proximity to the display. The proximity sensor may be an IR proximity sensor.

The display apparatus 100 may sense a gesture of selecting a partial area of a subject based on at least one of the photographed image and a sensing result of the proximity sensor.

Further, the display apparatus 100 may detect the position of a user present in front of the display based on least one of the photographed image and a sensing result of the proximity sensor, and based on the detected user position, it is determined on which position a mirror image is displayed, the mirror image which is created by light from the user being reflected.

Meanwhile, the display apparatus 100 may, if a user in front of the display is present within a certain distance, operate a magnifying function, and enlarge the body part which has approached the display. For example, the display apparatus 100 may detect eyes, a nose and a mouth of a user, and if it is determined that one of the body parts has approached the display closer than the other body parts, the display apparatus 100 may perform an image-processing of the photographed image so as to enlarge the closest body part, and display the processed image on the display. In this case, the enlargement rate may change based on the degree of a face and the distance between the display and the body part.

Also, the display apparatus 100 may detect a certain object from the photographed image, and activate a function associated with the detected object. For example, if a tooth brush has been detected, the display apparatus 100 may display a timer on the display, and if a smart watch has been detected, the display apparatus 100 may display health-related information on the display.

According to the various example embodiments described above, various user experiences may be provided by the display apparatus 100 which operates as a mirror and an image display apparatus.

Various example embodiments described above may be embodied in a recording medium that may be read by a computer or a similar apparatus to the computer by using software, hardware, or a combination thereof. According to the hardware embodiment, the example embodiments that are described in the present disclosure may be embodied by using at least one selected from a dedicated processor, a CPU, Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, electrical units for performing other functions. In some cases, example embodiments that are described in the present disclosure may be embodied as the processor 130. According to the software embodiment, embodiments such as processes and functions described in the present disclosure may be embodied as additional software modules. Each of the software modules may perform one or more functions and operations described in the disclosure.

The aforementioned method for controlling a display apparatus according to various example embodiments may be stored in a non-transitory computer readable medium and provided. The non-transitory computer readable medium may be mounted on various apparatuses.

A non-transitory computer readable medium is a medium that may perform a reading through a device. For example, the programs for performing the various methods described above may be stored in and provided through a non-temporary reading device such as a CD, a DVD, a hard disk, Blu-Ray, a disk, an USB, a memory card, a ROM and the like.

The foregoing example embodiments and advantages are merely examples and are not to be construed as limiting the example embodiments. The description of the example embodiments is intended to be illustrative, and not to limit the scope of the disclosure, as defined by the appended claims, and many alternatives, modifications, and variations will be apparent to those skilled in the art.

What is claimed is:

1. A display apparatus comprising:
a display configured to display a screen when the display is in a display mode and operate as a mirror when the display is in a mirror mode;
a camera configured to photograph an image; and
a processor configured to:
acquire a first image including a subject via the image having been photographed via the camera;
in response to a gesture selecting a part of the subject when the display is in a mirror mode, convert a first area of the display from the mirror mode into the display mode while a second area other than the first area is in the mirror mode;
control the display to display a second image including the selected part of the subject from the first image on the first area of the display and to display the first image on the second area other than the first area; and
switch the first area from a display mode displaying the second image into a mirror mode to operate as a mirror based on a determination that a distance between a body part of the second image and the display is equal to or greater than a predetermined distance.

2. The display apparatus of claim 1, wherein the processor is configured to control the display to display an image larger than a mirror image of the selected partial area on the first area.

3. The display apparatus of claim 1, further comprising:
a proximity sensor configured to sense an object within a predetermined proximity to the display,
wherein the processor is configured to sense the gesture based on at least one of the first image and a sensing result of the proximity sensor.

4. The display apparatus of claim 1, wherein the processor is configured to detect a plurality of body parts from the first image, to perform image-processing to highlight at least one of the plurality of detected body parts in the first image, and to control the display to display the processed image on a first area.

5. The display apparatus of claim 4, wherein the processor is configured to perform image-processing of the first image to highlight a body part closest to the display from among the plurality of detected body parts.

6. The display apparatus of claim 4, wherein the processor is configured to, in response to determining that a distance between the highlighted body part and the display is equal to or greater than a predetermined distance, control the display to operate the first area of the display as a mirror.

7. The display apparatus of claim 4, wherein the processor is configured to detect at least two of body parts from among eyes, a nose, a mouth and a head in the first image.

8. The display apparatus of claim 1, wherein the processor is configured to, in response to a gesture of moving the first area out of the display being received, control the display to operate the first area of the display as a mirror.

9. The display apparatus of claim 1, wherein the processor is configured to generate a capture image of a subject from the first image, and to control the display to display the generated capture image together with a pre-stored capture image regarding the subject.

10. The display apparatus of claim 1, wherein the processor is configured to, in response to a back view of a user being sensed, control the display to generate a capture image of the back view of the user, and in response to a front view of the user being sensed, to control the display to display the capture image of the back view of the user on the first area.

11. The display apparatus of claim 1, wherein the processor is configured to, in response to a video call function being performed, sense a position of a user, and based on the sensed position, to control the display to display an image of a counterpart which is received based on the video call function on an area in which a mirror image of the user is not displayed.

12. The display apparatus of claim 1, further comprising:
communication circuitry configured to communicate with an external electronic apparatus,
wherein the processor is configured to, in response to a user being detected from the photographed image, control the display to display an identification marker including communication information on an area in which a mirror image of the user is present, and to control the communication circuitry to connect to the electronic apparatus which has photographed the displayed identification marker.

13. The display apparatus of claim 12, wherein the processor is configured to, in response to a call being received in the electronic apparatus, and the electronic apparatus and the display apparatus being within a predetermined distance, control the display to display a UI element for receiving the call in the display apparatus.

14. The display apparatus of claim 12, wherein the processor is configured to, in response to a wearable device which collects user health information and stores the information in the electronic apparatus being detected in the photographed image, control the communication circuitry to receive the health information from the electronic apparatus, and to control the display to display the received health information.

15. The display apparatus of claim 1, wherein the processor is configured to identify a user from the photographed image based on pre-stored face information, and to control the display to display a content recommendation screen corresponding to the identified user.

16. The display apparatus of claim 1, wherein the display comprises:
a display panel configured to generate light corresponding to an image; and
a polarizing film disposed on a front side of the display panel, and configured to transmit light generated in the display panel and to reflect light incident from an outside.

17. A method for controlling a display apparatus comprising
a display configured to operate as a display screen in a display mode and as a mirror in a mirror mode, the method comprising:
generating a photographed image in which a subject is photographed;
acquiring a first image including the subject via the subject having been photographed;
in response to a gesture selecting a part of the subject when the display is in a mirror mode, convert a first area of the display from the mirror mode into the display mode while a second area other than the first area is in the mirror mode;
controlling the display to display a second image including the selected part of the subject from the first image on the first area of the display and to display the first image on the second area other than the first area; and
switching the first area from a display mode displaying the second image into a mirror mode to operate as a mirror based on a determination that a distance between a body part of the second image and the display is equal to or greater than a predetermined distance.

18. The method of claim 17, wherein the controlling comprises controlling the display to display in the first area an image larger than a mirror image of the selected part of the subject.

* * * * *